United States Patent [19]

Jenner et al.

[11] 4,362,869

[45] Dec. 7, 1982

[54] PROCESS FOR THE PREPARATION OF 4,1',6'-TRICHLORO-4,1',6'-TRIDEOXYGALACTOSUCROSE

[75] Inventors: Michael R. Jenner, Pangbourne; David Waite; Graham Jackson, both of Reading; John C. Williams, Wokingham, all of England

[73] Assignee: Talres Development (N.A.) N.V., Curacao, Netherlands Antilles

[21] Appl. No.: 212,898

[22] Filed: Dec. 4, 1980

[30] Foreign Application Priority Data

| Dec. 2, 1907 | [GB] | United Kingdom | 7943933 |
| Mar. 28, 1980 | [GB] | United Kingdom | 8010629 |
| Apr. 2, 1980 | [GB] | United Kingdom | 8011086 |
| May 20, 1980 | [GB] | United Kingdom | 8016668 |
| Nov. 14, 1980 | [GB] | United Kingdom | 8036711 |

[51] Int. Cl.$^3$ .............................................. C07H 1/00
[52] U.S. Cl. ...................................... 536/122; 536/125
[58] Field of Search ...................... 536/122, 17 R, 119

[56] References Cited

U.S. PATENT DOCUMENTS

| 4,008,218 | 2/1977 | Akita et al. | 536/17 |
| 4,117,224 | 9/1978 | Khan et al. | 536/122 |
| 4,262,115 | 4/1981 | Khan et al. | 536/122 |

OTHER PUBLICATIONS

Bredereck et al., "Chem. Ber.", vol. 91, 1958, pp. 2824–2829.

*Primary Examiner*—Johnnie R. Brown
*Attorney, Agent, or Firm*—Ostrolenk, Faber, Gerb & Soffen

[57] ABSTRACT

4,1',6'-trichloro-4,1',6'-trideoxygalactosucrose is prepared by a process including the steps of:
  (a) isomerizing 2,3,4,3',4'-penta-O-acetyl sucrose to 2,3,6,3',4'-penta-O-acetyl sucrose;
  (b) chlorinating the isomerized acetate at the 4,1' and 6'-positions; and
  (c) deacetylating the resulting chlorinated product; the isomerization step (a) being effected by treating a solution of 2,3,4,3',4'-penta-O-acetyl sucrose in an inert solvent with a weak acid at an elevated temperature.

12 Claims, No Drawings

PROCESS FOR THE PREPARATION OF 4,1',6'-TRICHLORO-4,1',6'-TRIDEOXYGALACTOSUCROSE

This invention relates to a process for the preparation of 2,3,6,3',4'-penta-O-acetyl sucrose and, hence, the preparation of the potent sweetner 4,1',6'-trichloro-4,1',6'-trideoxygalactosucrose or, properly, 1,6-dichloro-1,6-dideoxy-β-D-fructofuranosyl 4-chloro-4-deoxy-α-D-galactopyranoside. The above mentioned trichlorogalactosucrose, hereinafter referred to as TGS, is a potent sweetener having a sweetness several hundreds of times that of sucrose. Its use as a sweetener and sweetening compositions containing it are disclosed in British Patent Specification No. 1,543,167.

The main problem in the synthesis of TGS concerns the chlorination of the 4,1' and 6' positions of a sucrose molecule without chlorination at other positions. One way of achieving this is to chlorinate a sucrose derivative having the 2, 3, 6, 3' and 4' positions blocked, conveniently by esterification, so that only the 4,1' and 6' positions are available for chlorination. The chlorination of such an intermediate is complicated by the fact that, of the three hydroxy groups to be replaced by chlorine atoms, one is a reactive primary hydroxy group (the 6'-group), one is a considerably less reactive primary group (the 1'-group) and the third is a secondary hydroxy group.

The route disclosed in the literature (Fairclough et al., Carbohydrate Research, 40 (1975) 285-298) involves the formation of the 6,1',6'-tritrityl derivative of sucrose followed by peracetylation of the molecule. The tritrityl penta-acetate obtained is then, in one stage, de-tritritylated under conditions which cause a migration of the acetyl group at the 4-position to the 6-position vacated by one of the leaving trityl groups. This detritylation reaction was first reported by McKeown et al. (Canadian Journal of Chemistry 35 (1957) 28-36) and involves dissolving the tritrityl penta-acetate n glacial acetic acid and heating for the required time. Under these conditions, the yield of detritylated pentaacetate is generally not greater than about 55% of theory, the low yield apparently being caused by the formation of various competing by-products. MKeown et al. reported that an optimum yield could be achieved by refluxing for about 30 minutes. Any less or any more time led to a reduction in the yield, until at 120 minutes reflux substantially no desired product was obtained.

An alternative procedure for achieving the migration of the 4-acetyl group to the 6-position was demonstrated by Bredereck et al., (Chem.Ber.,) 91 (1958) 2824). In this two-stage procedure the tritrityl penta-acetate was first selectively detritylated by reaction with hydrogen bromide in acetic acid in the cold to give the non-isomerised penta-acetate. This, in turn, was treated with glacial acetic acid at an elevated temperature to obtain the isomerised penta-acetate in a relatively low yield (24%). The overall yield for the reaction from the tritrityl penta-acetate to the isomerised penta-acetate was about 19%.

From these publications, it appears that the combined detritylation and acetyl-migration gives a better yield of the isomerised penta-acetate than separate detritylation and subsequent isomerisation.

We have now found, surprisingly, that selection of specific reaction conditions for the acetyl migration step can give considerably higher yields overall for the two-stage process than the one-stage combined process.

According to the present invention, there is provided a process for the production of 4,1',6'-trichloro-4,1',6'-trideoxygalactosucrose including the steps of (a) isomerising 2,3,4,3',4'-pentaacetyl sucrose to 2,3,6,3',4'-penta-O-acetyl sucrose; (b) chlorinating the isomerised acetate at the 4,1' and 6'-positions; and (c) deacetylating the chlorinated product; characterised in that the isomerisation step (a) is effected by treating a solution of 2,3,4,3',4'-penta-O-acetyl sucrose in an inert solvent with a weak acid at an elevated temperature.

The weak acid is preferably a carboxylic acid, especially an aliphatic carboxylic acid such as acetic acid. In general any acid having an acid strength of the same order as acetic acid under the conditions used, will suffice.

The reaction temperature should be elevated above ambient temperature in order to provide an acceptable reaction time. In general, a temperature of from about 80° to 150° C. is suitable, preferably 100° to 130° C.

The inert solvent is any solvent for penta-O-acetyl sucrose which remains liquid at the elevated temperature selected, e.g. a temperature in the range of 100° to 140° C. Ketonic solvents are particularly preferred, especially methyl isobutyl ketone, which refluxes at about 126° C. Ester solvents of sufficiently high boiling point are also useful, e.g. n-butyl acetate. Also of particular interest are aromatic hydrocarbons such as toluene or xylene.

A dilute solution of the acid in the solvent is suitable, e.g. a solution of from 2 to 10% by weight, especially about 5%. This degree of dilution is suitable for reaction with the sucrose penta-acetate dissolved at a concentration of up to 30% by weight, e.g. about 20%.

The reaction time naturally depends on the temperature chosen, but at a temperature of about 110° to 130° C. a reaction of 2 to 4 hours has been found satisfactory.

In the reaction according to this invention, a yield of at least 75% of theory can be achieved in step (a). Since the detritylation of 6,1',6'-tritritylsucrose penta-acetate (without migration) can be achieved in well over 90% yield, this gives an overall yield from the tritrityl penta-acetate of about 70%. Detritylation of 6,1',6'-tritrityl sucrose pentaacetate can be effected simply by treatment with acid in an inert solvent at a low temperature, e.g. about 0° C. Thus, for example a ketonic solvent such as methyl isobutyl ketone in combination with glacial acetic acid, acidified further with a mineral acid such as hydrochloric acid, provides a convenient acid medium for the detritylation.

As explained earlier, another key process step in the synthesis of TGS involves the chlorination of 4, 1' and 6'-positions of the sucrose pentaacetate. It is necessary to use a chlorinating reagent which will effect chlorination at all three positions. Insufficient chlorination leads not only to a low yield, but also to a product comprising a mixture of chlorinated derivatives, which is difficult to separate. Many well-known chlorinating reagents used in the carbohydrate field are insufficiently active to provide a good yield of the trichloro derivative and the usual methods involves the use of sulphuryl chloride. This chlorinating reagent is used in a mixture of an organic amine base, such as pyridine, and a chlorinated hydrocarbon, such as chloroform. The reaction proceeds by formation of chlorosulphate esters which are then decomposed to form chloro derivatives. The method used by Fairclough et al., (op.cit.) involves the use of a small excess of sulphuryl chloride to ensure complete chlorination and a low temperature, e.g. −75° C. rising eventually to room temperature. We have now found that a greater excess of sulphuryl chloride (e.g. 2–5 ml per 1 g of sucrose pentaacetate as opposed to about 1 ml per 1 ml of pentaacetate) and a much higher reaction temperature (e.g. 20 up to about 55° C. or more) gives improved yields, typically about 75%.

According to a further feature of the present invention, there is provided a process for the production of TGS, as defined above, further characterised in that the chlorination step (b) is effected using 2 to 5 ml of sulphuryl chloride per 1 g of sucrose pentaacetate at a reaction temperature of from 20°–80° C.

However, one disadvantage of this process is the fact that the organic amine, especially pyridine, tends to be chlorinated by the sulphuryl chloride, leading to the formation of unwanted by-products which are difficult to separate. We have now found that certain other chlorinating reagents, which would not be expected to give the desired product, can in fact be used to give high yields in a simpler reaction procedure.

A class of chlorinating reagents derived from triarylphosphines and carbon tetrachloride is known in the art for chlorinating carbohydrates Usually, the reagent is used under relatively mild conditions in order to obtain selective chlorination of the more reactive primary hydroxy groups only. Thus, when one molar equivalent of the hydroxy compound is reacted with three molar equivalents of triphenylphosphine and 1.5 molar equivalents of carbon tetrachloride in pyridine at 0° C., sucrose yields 6,6'-dichloro-6,6'-dideoxysucrose; while uridine, methyl-α-D-glucopyranoside, inosine and other similar carbohydrates give chlorinated derivatives in which the primary hydroxy group has been replaced by a chlorine atom selectively (Kashem et al., Carbohydrate Research 61 (1978) 511-518). A reaction procedure of this type is the normal way in which the reagent is used and the reagent is generally regarded as a selective chlorinating agent for more reactive primary positions. Under more forcing conditions, i.e. more of the chlorinating agent and higher temperatures, sucrose is still not chlorinated at both of the 1'- and 4-positions together, but instead appears to be degraded.

A variation of the reagent is reported by Regen & Lee (J.Org.Chem. 40 1669-1670, 1975). In this case, one of the aryl substituents on the phosphine molecule is replaced by a styrene group of a cross-linked polystyrene. The reagent thus becomes, in effect, a resin-bound triarylphosphine, which behaves in the same way as an ordinary triarylphosphine. The great advantage of the "immobilized" reagent is that it can be easily removed from the reaction material (either unreacted or in the form of the triarylphosphine oxide by-product) and the by-product can be regenerated.

We have now found that a primary chlorinating reagent of the triarylphosphine/carbon tetrachloride type can be used to chlorinate 2,3,6,3',4'-penta-O-acetyl sucrose in the process for preparing TGS under conditions which would be expected to chlorinate the more reactive primary hydroxy groups only. Most surprisingly, the 1'-primary hydroxy group is replaced by a chlorine atom, unlike the 1'-hydroxy group in sucrose itself which does not react with this reagent, and the secondary 4-hydroxy group is also replaced by a chlorine atom, as is the 6'-hydroxy group.

According to a further feature of the present invention, the process according to the invention for the production of TGS as defined above is further characterised in that in step (b) the pentaacetate is reacted with a phosphine derivative of the general formula

$$P R^1 R^2 R^3 \qquad (I)$$

(where $R^1$ and $R^2$ represent aryl groups; and $R^3$ represents an aryl group or a resin-bound aryl group) in association with carbon tetrachloride, in an organic amine base, and at a temperature of from ambient to the reflux temperature of the system, preferably at a ratio of about 2 molar equivalents of phosphine derivative to 1 molar equivalent of carbon tetrachloride and preferably using at least 6 molar equivalent of phosphine derivative per molar equivalent of sucrose pentaacetate.

The phosphine derivatives may be divided into two types:
(a) those of Formula (I) in which $R^1$, $R^2$ and $R^3$ are all aryl groups, such as phenyl or alkylphenyl groups;
(b) those of Formula (I) in which $R^1$ and $R^2$ are as described for (a), while $R^3$ represents an aryl group bound to a resin, such as a phenyl group linked to a polymeric hydrocarbon, e.g. a phenyl group of a polystyrene resin.

A reagent of type (b) is described by Regen and Lee op.cit, namely polystyryldiphenylphosphine. This reagent may be regarded as triphenylphosphine bound by one phenyl group to a resin, or alternatively as a polystyrene resin of which a proportion of the phenyl groups are substituted with diphenylphosphino groups. This, and triphenylphosphine itself, are the reagents of choice.

The organic amine base is preferably a tertiary amine, especially a heterocyclic tertiary amine such as pyridine. In general, when using a ratio of 2 moles of phosphine derivative per mole of carbon tetrachloride in a base such as pyridine, the conditions are those which are well known in the prior art for selective chlorination at primary centres. Indeed, when these conditions are used on sucrose itself, only the 6- and 6'-positions are chlorinated. We have found, surprisingly, that at a temperature of from ambient to the reflux temperature of the system, this reagent will chlorinate at all three available centres of the sucrose pentaester, including the less accessible 1'-position and the secondary 4-position. The product is obtained in good yield and is substantially free of other chlorinated derivatives.

The reaction mixture may conveniently be worked up by adding a lower alkanol, such as methanol, to the reaction mixture and then evaporating the reaction mixture to dryness. The residue is then recrystallized from a suitable solvent after being washed with acid to remove basic materials. Where the phosphine derivative is resin-bound, the unreacted starting material and the phosphine oxide by-product can be removed simply by filtering the reaction mixture.

Another class of chlorinating agents which can be used in step (b) of the process of the present invention comprises the N,N-dialkyl(chloromethaniminium) chlorides of the general formula

$$[XClC\!=\!N^+R_2] Cl^- \qquad (II)$$

(where R represents an alkyl group, typically a methyl or ethyl group, and X represents a hydrogen atom or a methyl group).

Reagents of this type are prepared by reaction of an inorganic acid chloride with an N,N-dialkylformamide or N,N-dialkylacetamide. The inorganic acid chloride may typically be phosphorus pentachloride, phosgene, or thionyl chloride.

It is particularly surprising that this reagent will safely chlorinate in the 4,1'- and 6'-positions of a sucrose molecule as this class of acidic reagent is in general well known for its specificity as a chlorinator of more active primary hydroxy compounds. Thus, e.g. when N,N-dimethyl(chloromethaniminium) chloride was reacted with uridine, 5-chloro-uridine was obtained with no apparent chlorination in the two possible secondary positions (Dods & Roth, Tetrahedron Letters 165-168, 1969). Furthermore, reaction of a saccharide in which the primary hydroxy group and three of the four available secondary hydroxy groups had been protected by acetal formation to leave one free secondary hydroxy group yielded, in fact, a chlorinated product in which the primary hydroxy group had been replaced by chlorine, the protecting acetal having shifted to the secondary position. More specifically, 1,2:5,6-di-O-isopropylidene-α-D-glucofuranose gave 6-chloro-6-deoxy-1,2:3,5-di-O-isopropylidene-α-D-glucofuranose in a yield exceeding 70% (Hanessian and Plessas, J.Org.-Chem.34, 2163-2170, 1969).

We have now found that the reagents in question can be reacted with 2,3,6,3',4'-penta-O-acetylsucrose to give the corresponding trichloro derivative (i.e. TGS pentaacetate) in yields of well over 80%.

According to a further feature of the present invention, the process according to the invention for the production of TGS as defined above, is further characterised in that in step (b) the pentaacetate is reacted with a reagent of the formula

[XClC=N+R₂] Cl⁻      (II)

(where X represents a hydrogen atom or methyl group and R represents an alkyl group), formed by reaction of an inorganic acid chloride with an N,N-dialkylamide of the formula

R₂NCOX (where X and R are as defined above).

The reaction is preferably effected with a small excess of the chlorinating reagent (e.g. about 4 moles of reagent per mole of sucrose penta-ester) in an inert solvent. The inert solvent may be, for example, a chlorinated hydrocarbon such as 1,2,2-trichloroethane or an aromatic hydrocarbon solvent such as toluene. The reaction is conveniently effected under reflux and preferably under a nitrogen atmosphere to maintain dry reaction conditions. The reaction mixture can be very simply worked up by evaporation to dryness and recrystallization from a solvent such as ethanol, desirably with a colour-removal step, such as a filtration through charcoal.

The reagent of formula (II) is conveniently formed in situ in the reaction vessel by direct contact of the inorganic acid chloride with the amide. Alternatively, the reagent may be formed beforehand and added as such to the reaction vessel. Formation of the reagent may be achieved by reaction of the acid chloride, e.g. phosphorus pentachloride or thionyl chloride, with the amide, conveniently either in approximately stoichiometric amounts or using an excess of the amide as solvent. Alternatively, since the amide is regenerated during the chlorination reaction, it is possible to use the required amount of the acid chloride and a "catalytic" amount of the amide, so that the chlorinating reagent is constantly being re-formed during the reaction.

This chlorination process thus provides a simple, rapid and easily worked-up reaction giving high yields of the desired chlorinated sucrose ester.

Yet another class of chlorinating agents of use in step (b) of the process of the present invention comprises the tri-substituted dichlorophosphoranes which can give high yields of product, often at ordinary room temperatures, in a selective and rapid manner.

According to a yet further feature of the present invention, the process according to the invention for the production of TGS by the method described above is further characterised in that the pentaacetate is reacted with a dichlorophosphorane derivative of the general formula

Y₃PCl₂      (III)

(in which Y represents an aryl group, e.g. a substituted or unsubstituted phenyl group especially an unsubstituted phenyl group, or an aryloxy group, e.g. a substituted or unsubstituted phenoxy group, especially an unsubstituted phenoxy group).

Reagents of the formula (III) in which Y represents an aryloxy group, may be prepared by reaction of a triaryl phosphite of the general formula Y₃P (where Y is an aryloxy group) with gaseous chlorine. This reaction can be effected simply by bubbling the chlorine gas into the liquid triaryl phosphite. Alternatively, the gas may be bubbled into a solution of the triaryl phosphite in an inert solvent. Reagents of the formula (III) in which Y represents an aryl group may similarly be prepared by reaction of a triarylphosphine of the general formula Y₃P (where Y is an aryl group), with chlorine gas. In this case, however, a solvent for the triarylphosphine is desirable, for example a chlorinated hydrocarbon such as carbon tetrachloride, which can subsequently be evaporated off before the reagent is used.

Triaryloxydichlorophosphoranes are a known class of compounds. Thus, for example, triphenoxydichlorophosphorane has been given the CAS Registry number 15493-07-9 by Chemical Abstracts and was reported by Coe et al. (J.Chem.Soc.1954 p 2281) to be a good chlorinating reagent for alcohols. However, this compound has been reported (Osake Kogyo Gijutsu Shikensho Kiho, 1967, 18, 117-122) to produce polymers when condensed with dihydroxy compounds. It is thus surprising that this class of reagent will safely chlorinate the three hydroxy groups of the above-mentioned sucrose pentaacetate.

Triaryldichlorophosphoranes are also a known class of compound. Triphenyldichlorophosphorane has the Chemical Abstracts CAS Registry Number 2526-64-9 and has been reported, for example by Wiley et al., J. Am.Chem.Soc 86, 964, (1964), as a chlorinating agent for alcohols. It has also been used for the cleavage of ethers and the chlorination of aldehydes and ketones and might thus be expected to be unsafe for the chlorination of sucrose derivatives.

The reagent of formula III is preferably formed immediately before use by chlorination of a triaryl phosphite or triarylphosphine as described above. The chlorination of the sugar ester is conveniently effected in a basic solvent, e.g. a tertiary amine such as pyridine. The reaction with a triaryloxydichlorophosphorane can conveniently be effected at ambient temperature or above e.g. 15°–60° C., possibly with cooling if necessary, since the reaction is mildly exothermic; the reaction with a triaryldichlorophosphorane, however, needs a higher temperature, e.g. from 50°–95° C.

The reaction mixture can conveniently be worked up by pouring it into water and extracting with an organic solvent such as dichloromethane. The extracts, when washed with acid and with base, dried and evaporated, yield a product which can be further purified by chromatography, for example on silica gel, to give a yield of the tri-chlorinated ester of approaching 80%.

The following examples illustrate the invention further. All temperatures are in degrees Celsius. Amberlite and Amberlyst are registered Trade Marks.

EXAMPLE 1

Preparation of 2,3,6,3',4'-Penta-O-Acetyl Sucrose (Starting Material)

(a) Using Methyl Isobutyl Ketone 2,3,4,3',4'-penta-O-acetyl sucrose (2 g) was dissolved in methyl isobutyl ketone (20 ml) and acetic acid (1 ml) was added. The reaction of the mixture was heated under reflux (about 126°) for 3 hours. On cooling, the product crystallized to give a yield of 1.5 g (75%) of 2,3,6,3',4'-penta-O-acetyl sucrose.

(b) Using Toluene 2,3,4,3',4'-Penta-O-acetylsucrose (2 g; purity 83.63%) and glacial acetic acid (0.2 liter) were added to toluene (10.0 liter) and the mixture was heated to reflux and maintained at reflux for 6 hours or until the acetyl migration was completed. The solution was cooled to ambient temperature and the precipitate filtered off, washed with fresh toluene and dried in a vacuum oven at 40° C. to give 2,3,6,3',4'-penta-O-acetylsucrose (15.90 g; purity 87.65%) in an overall yield of 83.3%

EXAMPLE 2

Preparation of 4,1',6'-Trichloro-4,1',6'-Trideoxygalactosucrose

Step 1

Tritylation and Acetylation

Sucrose (100 g) and trityl chloride (270 g) were added to dry pyridine (600 ml) and stirred with heating at 65° for 18 hours. Pyridine was then removed under vacuum and the syrupy product was acetylated by the addition of acetic anhydride (600 ml) with stirring at room temperature for 12 hours. The reaction mixture was then poured into ice water with stirring and the precipitated product filtered off and dried to constant weight. A solution of this precipitate in dichloromethane (1 liter) was dried over sodium sulphate and concentrated to a syrup which was repeatedly dissolved in methanol, diluted with toluene and concentrated, to remove traces of pyridine. The product was then crystallised from acetone-methanol (1:9, 500 ml) at 0° to give 6,1',6'-tri-O-tritylsucrose penta-acetate (260 g, 70%).

Step 2a

Detritylation 6,1',6'-Tri-O-tritylsucrose penta-acetate (50 g) was dissolved in dichloromethane (500 ml) and acetic acid (500 ml) and the solution was cooled to 0° and concentrated hydrochloric acid (10 ml) was added thereto. The reaction mixture was stirred at 0° for 2 hours, and then neutralised by the addition of Amberlite IR 45 (OM) resin. The reaction mixture was stirred for 1 hour, concentrated to a syrup, and methanol (200 ml) was added. After 3 hours at 0°, the triphenylmethanol (27.6 g 96%) which had precipitated was filtered off and the solution was concentrated to a syrup. Acetone (400 ml) was added and the solution was decolorised with charcoal and then concentrated to a thin syrup. Ether (300 ml) was added and 2,3,4,3',4'-penta-O-acetylsucrose crystallised out at room temperature. (Yield: 20.5 g, 95%).

Step 2b

Acetyl migration 2,3,4,3',4'-Penta-O-acetylsucrose (20 g) was dissolved in methyl isobutyl ketone (200 ml) and acetic acid (10 ml) was added. The reaction mixture was heated under reflux at 125° for 2.75 hours. The reaction mixture was then cooled to 60° and petroleum ether (60°–80°) (200 ml) was added. On further cooling, 2,3,6,3',4'-penta-O-acetylsucrose crystallised out. After 16 hours at 0°, the crystalline product was filtered off, washed with diethyl ether and dried.

Yield = 15.2 g (75%).

Step 3

Chlorination with sulphuryl chloride

A solution of sulphuryl chloride (15 ml) in 1,2-dichloroethane (15 ml) was added to a solution of 2,3,6,3',4'-penta-O-acetylsucrose (5 g) in pyridine (15 ml) and 1,2-dichloroethane (15 ml) without external cooling. An exothermic reaction caused the temperature to increase to 45°–55°. The reaction mixture was heated under reflux for 4 hours, then cooled and dichloroethane (50 ml) was added. The resulting solution was washed successively with 10% hydrochloric acid (100 ml), water, and 10% sodium hydrogen carbonate solution to neutrality. The organic phase was dried, concentrated to a syrup and crystallised from toluene (25 ml) to give 4,1',6'-trichloro-4,1',6'-trideoxygalactosucrose penta-acetate.

Yield = 4.1 g (75%).

Step 4

De-acetylation 4,1',6'-Trichloro-4,1',6'-trideoxygalactosucrose penta-acetate (20 g) was dissolved in methanol (200 ml), and 1.0.N sodium methoxide in methanol was added until pH 9. The reaction mixture was stirred at room temperature for 4 hours, then neutralised with Amberlyst 15 (H+) ion exchange resin, filtered and concentrated to dryness. The solid product was dissolved in distilled water (60 ml) giving a cloudy solution which was filtered to give a clear colourless solution. The aqueous solution of TGS was then concentrated to dryness.

Yield = 12.6 g (96%)

The overall yield from sucrose was 36%.

EXAMPLE 3

Chlorination Using Polymer-Bound Triphenylphosphine

To a suspension of polymer-bound triphenylphosphine (Regen & Lee J.Org.Chem 40 (1975) 1669) (8 g, 6 molecular equivalents assuming approximately 80% substitution) in pyridine (38 ml) at 0° was added carbon tetrachloride (2 g, 3 molecular equivalents) followed by 2,3,6,3',4'-penta-O-acetyl sucrose (2.3 g, 1 molecular equivalent).

The mixture was then heated to 80° for four hours, cooled and filtered. The polymer beads were washed with dichloromethane and the combined filtrate and washings were evaporated to dryness. The residue was dissolved in dichloromethane and the solution was washed successively with 1 molar hydrochloric acid, saturated aqueous 1 molar hydrochloric acid, saturated aqueous sodium hydrogen carbonate and water and was then dried over sodium sulphate. The solution was then filtered through charcoal and evaporated to give 2.3 g of crude trichloro product. A crystallization of the crude product from ethanol gave 1.4 g (67%) of crystalline 4,1',6'-trichloro-4,1',6'-trideoxy-2,3,6,3',4'-penta-O-acetyl-galactosucrose. Further material was obtainable from the mother liquor.

EXAMPLE 4

Chlorination Using Triphenylphosphine

To a solution of 2,3,6,3',4'-penta-O-acetyl-sucrose (4.9 g 1 molecular equivalent)in pyridine (100 ml) was added at 0°, triphenylphosphine (13.1 g 6 molecular equivalents),followed by carbon tetrachloride (3.9 g 3 molecular equivalents). The mixture was heated at about 70° for 3 hours and then cooled. Methanol (120 ml) was added to the cooled mixture, which was worked up by evaporating to dryness, dissolving the residue in methylene chloride, washing successively with 1 M HCl and NaHCO$_3$ solutions, drying with Na$_2$SO$_4$, filtering through charcoal and finally evaporating again to give a syrup. Acetone was added to the residue and any undissolved material was filtered off. The solution was again evaporated and the residue crystallized from ether. These crystals contained no sugary material and were discarded, while the solution was evaporated and then crystallized from ether/petrol to give 3.4 g(60%) of trichlorosucrose pentaacetate, slightly contaminatd with triphenylphosphine oxide. Recrystallization gave the pure product (2.3 g, 40%).

EXAMPLE 5

4,1',6'-Trichloro-4,1',6'-Trideoxygalactosucrose 2,3,6,3',4'-Penta-O-Acetate From Reagent Derived From PCl$_5$ and Dimethylformamide Phosphorus pentachloride (50 g, 0.24 mole) was added in small portions to DMF (140 g, 1.92 moles) with stirring, during which the temperature rose to about 120° C. The mixture was then cooled to 0° C. and the N, N-dimethyl-chloromethaniminium chloride crystallised out and was filtered off. (See Hepburn and Hudson, J. C. S. Perkin 1, 754, 1976). To 1,1,2-trichloroethane (120 ml) was added N,N-dimethyl-chloromethaniminium) chloride (14 g, 4 molecular equivalents). This mixture was cooled to 0° C., and 2,3,6,3',4'-penta-O-acetylsucrose (15 g, 1 molecular equivalent) was then added, and the combined mixture was stirred and refluxed under nitrogen for 4 hours and then allowed to cool. The cooled reaction mixture was filtered through a charcoal pad, which was then washed with dichloromethane. The combined filtrate and washings were then evaporated to dryness and the residue was recrystallized from ethanol to give 13.45 g (82%) of the trichloro pentaacetate

EXAMPLE 6

Reaction of 2,3,6,3',4'-Penta-O-Acetyl Sucrose With Vilsmeier Reagent Derived From Thionyl Chloride and DMF Thionyl chloride (8.5 ml) was added to DMF (8.4 ml) which became hot and the mixture was evaporated under vacuum at 50° to give a syrup. To this was then added 1,1,2-trichloro-ethane (120 ml) and the mixture was cooled to 0°. Sucrose 2,3,6,3',4'-pentaacetate (15 g) was added and this mixture was refluxed for 3 hours, cooled and filtered through charcoal and the red-brown filtrate was evaporated to dryness. The resulting syrup was crystallized from ethanol to give 11.8 g (72%) of slightly coloured crystals. A recrystallization then gave 10.9 g (70%) of almost colourless crystalline trichloro-sucrose pentaacetate.

EXAMPLE 7

Preparation of 4,1',6'-Trichloro-4,1',6'-Trideoxygalactosucrose Pentaacetate Using a Vilsmeier Reagent Formed in Situ.

2,3,6,3',6'-Penta-O-acetylsucrose (5 g, purity 80%) was dissolved in a mixture of toluene (40 ml) and dimethylformamide (8.6 ml). A solution of thionyl chloride (8.3 ml) in toluene (15 ml) was added gradually to the stirred reaction mixture over a period of 15 minutes during which the temperature rose to 40° C. Upon completion of the addition, the mixture was stirred for a further 15 minutes and then heated to reflux and refluxed for 5 to 6 hours. The course of the reaction was monitored by thin layer chromatography. When the reaction was complete, charcoal was added and the warm mixture was stirred for 20 minutes and then filtered through a filter-pad. The residue remaining in the flask was washed with a little toluene which was also filtered. The combined filtrates and washings were evaporated and the residue crystallised from toluene (20 ml) to give 4,1',6'-trichloro-4,1',6'-trideoxygalactosucrose penta-acetate (4.32 g; priority 85.5%) in an overall yield of 84%.

EXAMPLE 8

Reaction of 2,3,6,3',4'-Penta-O-Acetyl Sucrose With Vilsmeier Reagent Derived From Thionyl Chloride and a Catalytic Amount of DMF To sucrose 2,3,6,3',4'-pentaacetate (2.75 g) in 1,1,2-trichloroethane (20 ml) was added DMF(approx. 0.15 ml) and the mixture brought to reflux. Thionyl chloride (1.7 ml) in 1,1,2-trichloroethane (10 ml) was added over approx. 45 minutes and the mixture refluxed for a further 5 hours. A further 0.15 ml DMF and 1 ml sulphuryl chloride was added at once to the mixture, which was refluxed for a further 3 hours.

The black reaction mixture was filtered through charcoal and the brown-red filtrate was evaporated to give a syrup which was crystallized from ethanol to give 6.3 g (40%) of trichloro sucrose pentaacetate as off-white crystals.

EXAMPLE 9

Chlorination of Sucrose 2,3,6,3',4'-Penta-O-Acetate Using Triphenoxydichlorophosphorane Chlorine gas was bubbled into triphenyl phosphite (3.1 g, 2.6 ml, 4 molar equivalents) (supplied by Aldrich Chemical Co.Ltd.) with stirring until a weight increase of 0.7 g was observed. The liquid became quite hot during the addition of chlorine and solidified on cooling. The cooled material was dissolved in pyridine (20 ml) and the sucrose 2,3,6,3',4'-pentaacetate (1.4 g, 1 molar equivalent) was added and dissolved. A crystalline precipitate formed almost immediately and, the mixture became quite warm. After 10 minutes, a sample showed on t.l.c. (ether/petrol) a single major product (R$_f$0.5) corresponding to the pentaacetate of TGS together with two minor components (R$_f$0.3 and 0.0). The mixture was stirred for a further hour and then poured into water and extracted with dichloromethane. The extract was washed with 0.1 N HCl and with sodium hydrogen carbonate solution and then dried (sodium sulphate), filtered through charcoal and evaporated to give a pale yellow syrup. This syrup was chromatographed on a column of silica gel, eluted with diethyl ether/40°-60° petroleum ether (4:1), to give TGS pentaacetate (1.2 g 78%) which was crystallized from ethanol and found to be identical with an authentic sample.

EXAMPLE 10

Chlorination of Sucrose 2,3,6,3',4'-Penta-O-Acetate Using Triphenyldichlorophosphorane Chlorine gas was bubbled into a solution of triphenylphosphine (5.6 g) 8 ME) in carbon tetrachloride (20 ml) at 0° with stirring until a weight increase of 1.4 g was observed. Care was taken not to let the inlet tube get blocked with the reagent that was formed during the reaction. Some external cooling was applied as the reaction mixture became quite hot. The remaining solvent was evaporated and the residue dissolved in pyridine (10 ml). Sucrose pentaacetate (1.4 g, 1 ME) was added to this stirred solution and it dissolved with slight evolution of heat. The solution was left at room temperature for 2½ hours and then was heated to 55° for 2 hours and then 85° for 3 hours, by which time the mixture had become very dark. T.l.c. analysis (ether/petrol 4:1) now indicated that a single compound (R$_f$0.5) was present corresponding to TGS pentaacetate. The pyridine was evaporated and the residue was dissolved in dichloromethane and washed with 0.1 N HCl, and NaHCO$_3$ solution, then dried (sodium sulphate), filtered through a charcoal pad to give a colourless filtrate and evaporated to give 6.5 g of a syrup. This was chromatographed as in Example 8 to give 1.1 g TGS pentaacetate, which crystallized from ethanol in 75% yield.

We claim:

1. In a process for the production of 4,1',6'-trichloro-4,1',6'-trideoxygalactosucrose including the steps of (a) isomerising 2,3,4,3',4'-penta-O-acetyl sucrose to 2,3,6,3',4'-penta-O-acetyl sucrose; (b) chlorinating the isomerised acetate at the 4,1', and 6'-positions and (c) deacetylating the chlorinated product, the improvement comprising effecting the isomerisation step (a) by treating a solution of 2,3,4,3',4'-penta-O-acetyl-sucrose in an inert solvent with a weak acid having an acid strength on the same order as acetic acid at an elevated temperature of at least about 80° C.

2. A process according to claim 1, in which the acid is acetic acid.

3. A process according to claim 1, in which the temperature is from 80° to 150° C.

4. A process according to claim 1, in which the sucrose pentaacetate is at a concentration of up to 30% by weight and the acid concentration is from 2 to 10% by weight.

5. A process according to claim 1, further improved by effecting the chlorination in step (b) by reacting the sucrose pentaacetate with 2 to 5 ml of sulphuryl chloride per 1 g of sucrose pentaacetate at a reaction temperature of from 20° to 80° C.

6. A process according to claim 1, further improved by effecting the chlorination in step (b) by reacting the sucrose pentaacetate with a phosphine derivative of the general formula:

$$P\ R^1R^2R^3$$

(where R$^1$ and R$^2$ represent phenyl groups and R$^3$ represents a phenyl group or a polystyrenebound phenyl group) and carbon tetrachloride; in an organic tertiary amine base and at a temperature of from ambient to the reflux temperature of the system.

7. A process according to claim 6, in which R$^1$ and R$^2$ represent phenyl groups and R$^3$ represents a phenyl group or a polystyrene-linked phenyl group.

8. A process according to claim 1, further improved by effecting the chlorination in step (b) by reacting the sucrose pentaacetate with a reagent of the general formula:

$$[X\ ClC=^+NR_2]\ Cl^- \qquad (II)$$

(in which X represents a hydrogen atom or a methyl group and R represents an alkyl group) in an inert solvent.

9. A process according to claim 8 in which the reagent of formula (II) is obtained by reacting thionyl chloride with N,N-dimethyl formamide.

10. A process according to claim 1, further improved by effecting the chlorination in step (b) by reacting the sucrose pentaacetate with a reagent of the general formula:

$$Y_3PCl_2 \qquad (III)$$

(in which Y represents an aryl group or an aryloxy group).

11. A process according to claim 10, using a reagent of the formula (III) in which Y represents a phenyl group or a phenoxy group.

12. A process according to claim 1 in which the temperature is 100°-130° C.

* * * * *